(12) United States Patent
Na et al.

(10) Patent No.: US 9,360,461 B2
(45) Date of Patent: Jun. 7, 2016

(54) ACOUSTIC COUPLING SHOES FOR USE IN INSPECTING NON-FLAT SURFACES

(71) Applicants: Jeong Na, Dayton, OH (US); Sean Gleeson, Upper Arlington, OH (US)

(72) Inventors: Jeong Na, Dayton, OH (US); Sean Gleeson, Upper Arlington, OH (US)

(73) Assignee: EDISON WELDING INSTITUTE, INC., Columbus, OH (US)

( * ) Notice: Subject to any disclaimer, the term of this patent is extended or adjusted under 35 U.S.C. 154(b) by 259 days.

(21) Appl. No.: 13/922,869

(22) Filed: Jun. 20, 2013

(65) Prior Publication Data

US 2014/0375169 A1   Dec. 25, 2014

Related U.S. Application Data

(60) Provisional application No. 61/662,717, filed on Jun. 21, 2012.

(51) Int. Cl.
*G01N 29/28*  (2006.01)
*G01N 29/34*  (2006.01)

(52) U.S. Cl.
CPC ............... *G01N 29/34* (2013.01); *G01N 29/28* (2013.01); *G01N 2291/2634* (2013.01)

(58) Field of Classification Search
CPC ..... G01N 29/34; G01N 29/28; G01N 29/221; G01N 29/262; G01N 29/2487; G01N 29/041; G01N 2291/2634; H01L 41/09; H01L 41/0825

USPC ......... 73/643, 644, 637, 638, 642; 310/313 B
See application file for complete search history.

(56) References Cited

U.S. PATENT DOCUMENTS

| | | | | |
|---|---|---|---|---|
| 4,195,530 | A * | 4/1980 | Ross et al. ....................... | 73/638 |
| 4,372,163 | A * | 2/1983 | Tittmann et al. ................ | 73/602 |
| 4,462,256 | A * | 7/1984 | Moffett ........................... | 73/642 |
| 4,462,257 | A * | 7/1984 | Gerhart et al. .................. | 73/644 |
| 5,367,216 | A * | 11/1994 | Egara et al. ............... | 310/313 R |
| 6,575,043 | B1 * | 6/2003 | Huang et al. ............... | 73/861.25 |
| 6,718,268 | B2 * | 4/2004 | Fantana et al. ................... | 702/41 |
| 7,516,664 | B2 * | 4/2009 | Meier et al. ..................... | 73/644 |
| 8,047,081 | B2 * | 11/2011 | Berberig et al. ........... | 73/861.25 |
| 2004/0016299 | A1 * | 1/2004 | Glascock et al. .............. | 73/638 |
| 2006/0169837 | A1 * | 8/2006 | Bird et al. .................... | 244/99.8 |
| 2007/0039371 | A1 * | 2/2007 | Omata et al. ........................ | 73/9 |
| 2007/0107519 | A1 * | 5/2007 | Liu et al. ......................... | 73/649 |

* cited by examiner

*Primary Examiner* — Helen Kwok
(74) *Attorney, Agent, or Firm* — McNees Wallace & Nurick, LLC

(57) ABSTRACT

A system for inspecting the surface of a curved object is provided. This system includes an object having a curved surface; at least one substantially flat interdigital transducer, wherein the interdigital transducer is operative to generate surface energy waves; and at least one coupling device disposed between the curved surface and the substantially flat interdigital transducer, wherein the coupling device is operative to conform to the curved surface, support the interdigital transducer, and provide a medium through which the surface energy waves can effectively travel from the interdigital transducer to the curved surface and across the curved surface in a predetermined direction.

24 Claims, 5 Drawing Sheets

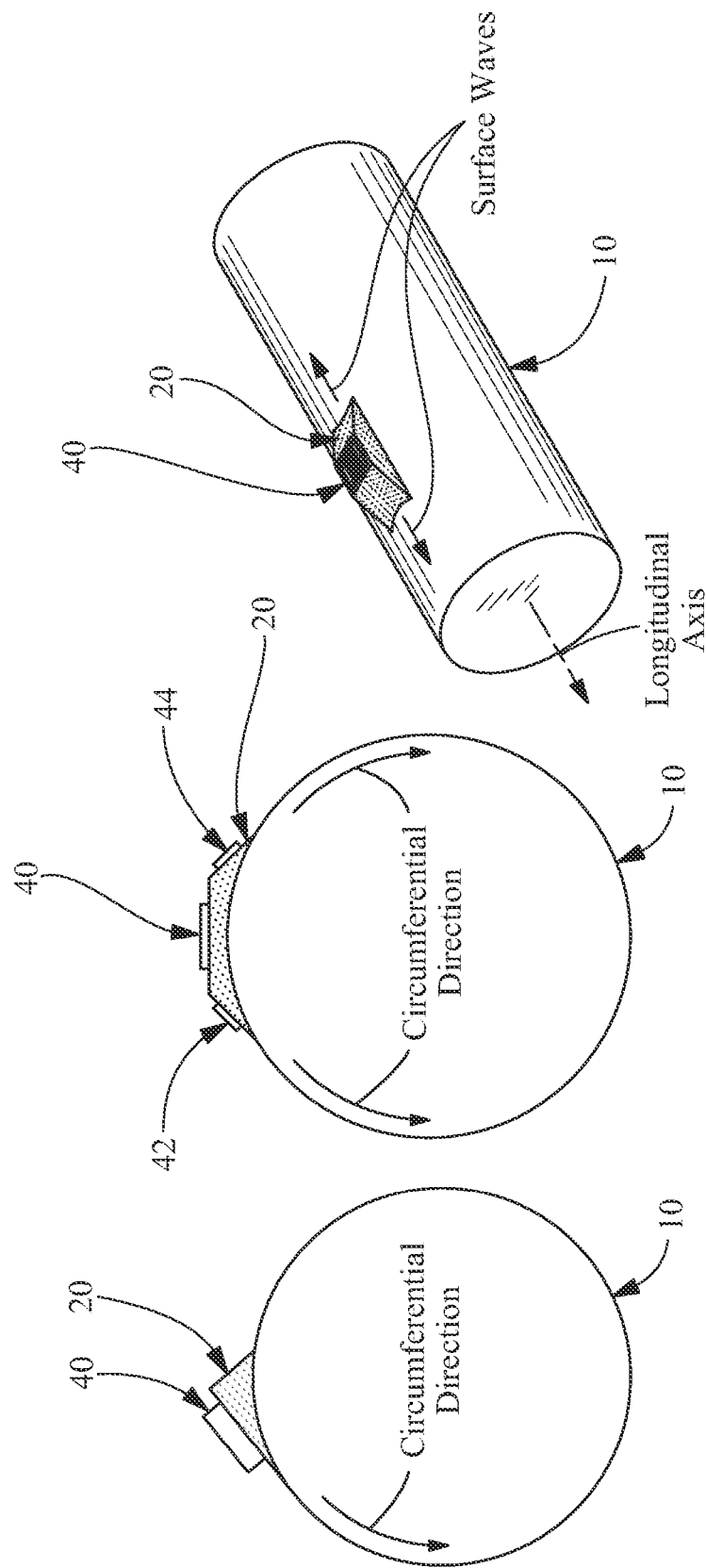

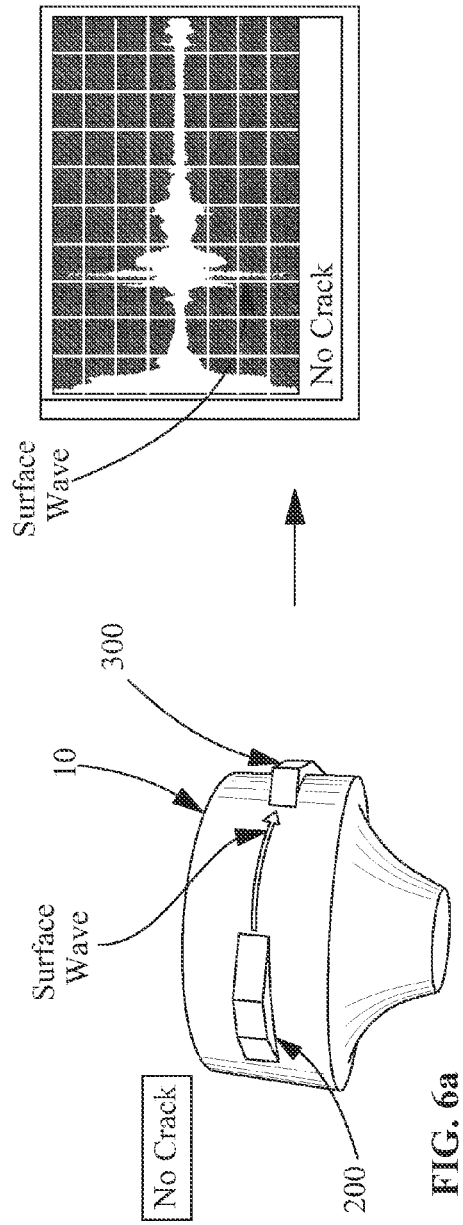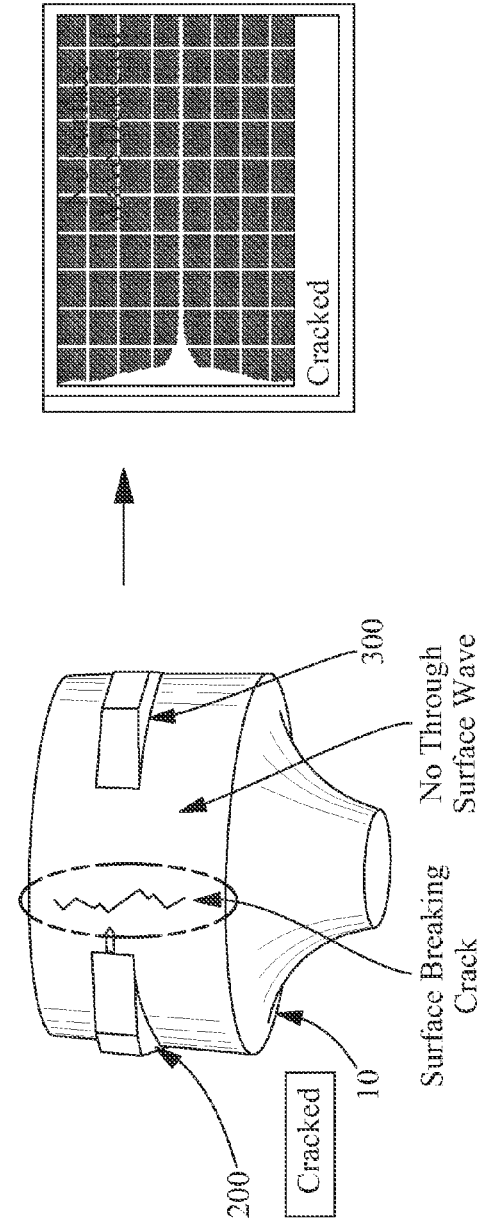
FIG. 6a
FIG. 6b

ACOUSTIC COUPLING SHOES FOR USE IN INSPECTING NON-FLAT SURFACES

CROSS-REFERENCE TO RELATED APPLICATIONS

This patent application claims the benefit of U.S. Provisional Patent Application Ser. No. 61/662,717 filed on Jun. 21, 2012 and entitled "Acoustic Coupling Shoes for Use in Inspecting Non-Flat Surfaces", the disclosure of which is hereby incorporated by reference herein in its entirety and made part of the present U.S. utility patent application for all purposes.

BACKGROUND OF THE INVENTION

An interdigital transducer, interdigitized transducer, or interdigitated transducer, is a device or sensor which typically consists of two interlocking comb-shaped metallic coatings or structures that have been applied to a piezoelectric substrate, such as quartz, lithium niobate, or piezoelectric ceramics, for the purpose of converting electrical or electromagnetic energy (e.g., microwaves) into acoustic energy (e.g., surface acoustic waves (SAW)) or vice versa. Interdigital transducers may be used to generate and receive ultrasonic surface waves for the purpose of inspecting the surface condition of a particular item or for measuring its acoustic properties.

Currently, there are no known effective means for transferring surface waves generated by a flat interdigital transducer to a curved, contoured, or otherwise non-flat surface of an object. A custom-designed curved interdigital transducer may be fabricated for use on a curved surface of a part being inspected. However, creating complex contoured interdigital transducers is difficult and increases manufacturing costs considerably. Furthermore, a custom-designed interdigital transducer or sensor is only compatible with the specific contoured part or surface for which the sensor was originally designed. Accordingly, there is a need for a means by which flat interdigital transducers or sensors may be easily and inexpensively adapted for use with curved or contoured items that are to be inspected.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a first system for inspecting the surface of a curved object is provided. This system includes at least one object having a curved surface; at least one substantially flat interdigital transducer, wherein the interdigital transducer is operative to generate surface energy waves; and at least one coupling device disposed between the curved surface and the substantially flat interdigital transducer, wherein the coupling device is operative to conform to the curved surface, support the interdigital transducer, and provide a medium through which the surface energy waves can effectively travel from the interdigital transducer to the curved surface and across the curved surface in a predetermined direction.

In accordance with another aspect of the present invention, a second system for inspecting the surface of a curved object is provided. This system includes at least one object having a curved surface; at least one substantially flat interdigital transducer, wherein the interdigital transducer is operative to generate and receive surface acoustic waves; and at least one coupling device disposed between the curved surface and the substantially flat interdigital transducer, wherein the coupling device is operative to conform to the curved surface, support the interdigital transducer, and provide a medium through which the surface acoustic waves can effectively travel from the interdigital transducer to the curved surface and across the curved surface in a predetermined direction.

In yet another aspect of this invention, a coupling device for transmitting surface energy waves is provided. This device includes a substantially flat top surface, wherein the substantially flat top surface is adapted to receive at least one surface energy wave generating device; a curved bottom surface, wherein the curved bottom surface is of greater length than the top surface and is adapted to conform to a curved surface of an object to be inspected; and a least two angled side surfaces between the top and bottom surfaces, wherein the angled side surfaces are operative to direct surface energy waves generated by the at least one surface energy wave generating device onto and across the curved surface of an object to be inspected.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein:

FIGS. 4a-c illustrate different possible mounting positions and alternate geometric configurations for the coupling shoes of the present invention;

FIGS. 6a-b illustrates the inspection results of cylindrically shaped test samples; one with no crack and the other with a surface breaking crack occurring on the side wall section thereof.

DETAILED DESCRIPTION OF THE INVENTION

Exemplary embodiments of the present invention are now described with reference to the Figures. Although the following detailed description contains many specifics for purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

With reference to the Figures, this invention provides various interchangeable devices that effectively accommodate single or multiple substantially flat interdigital transducers (also referred to as "sensors") and which operate to transfer surface wave energy generated by the interdigital transducer(s) to one or more non-flat surfaces of a part to be inspected or otherwise analyzed. The devices of the present invention, which are referred to as "acoustic coupling shoes", are operative to eliminate air gaps that typically occur between the curved surface of a part to be inspected and a flat or substantially flat interdigital transducer (IDT). The acoustic coupling shoes of this invention may be manufactured from any number of materials, such as polymethyl methacrylate (PMMA), that will: (i) support an IDT sensor or similar device; (ii) uniformly contact a contoured surface of a part; and (iii) effectively transmit and/or receive surface acoustic waves or similar energy. Once surface wave energy has been transferred onto a curved surface of a part using such coupling shoes, that energy can then be used for inspecting surface conditions or measuring material properties of the item. This invention provides an acoustic coupling system and devices for both transmission and reception of surface waves induced by IDT sensors for use with non-flat surfaces.

Figure 1:
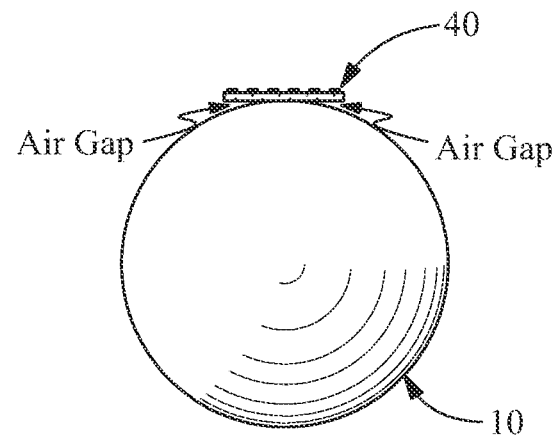
FIG. 1 illustrates the appearance of a flat interdigital transducer placed on the curved surface of a part to be tested or analyzed.
Figure 2:
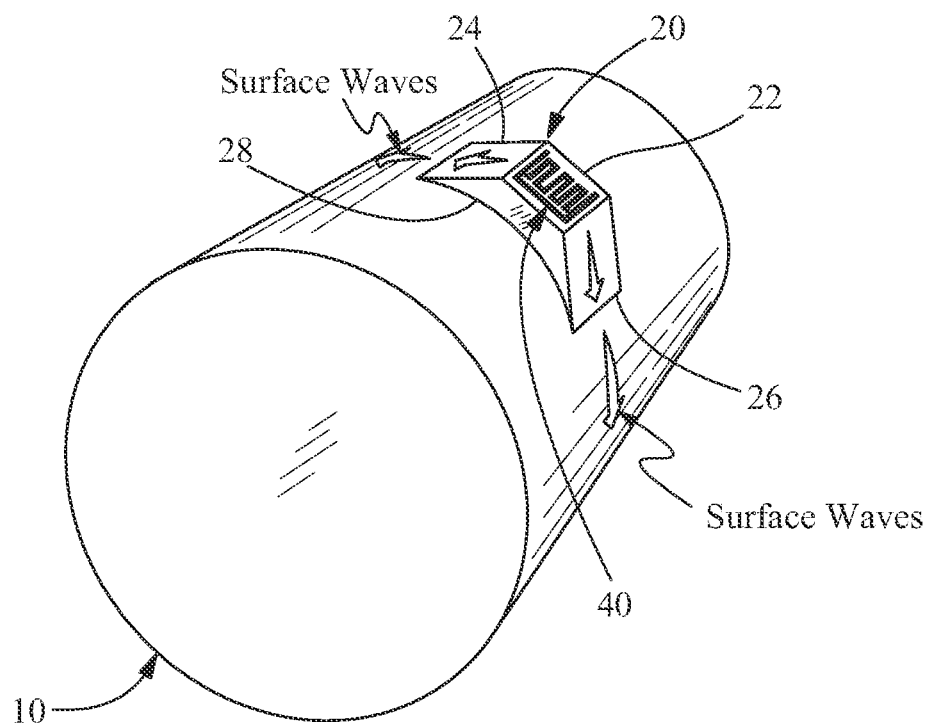
FIG. 2 illustrates the appearance of a flat interdigital transducer that has been mounted on the substantially flat top surface of an exemplary embodiment of the coupling shoes of present invention for purposes of dramatically increasing the contact surface between the curved part and the interdigital transducer.
Figure 3A:
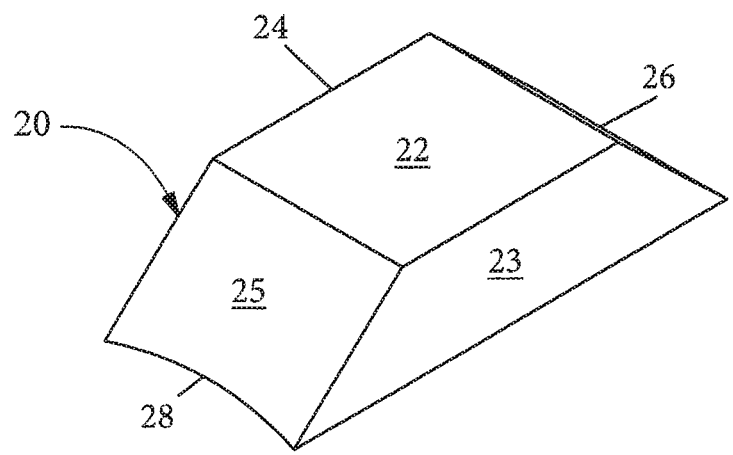
FIGS. 3a-b illustrate two possible geometries for the coupling shoes of the present invention.
Figure 3B:
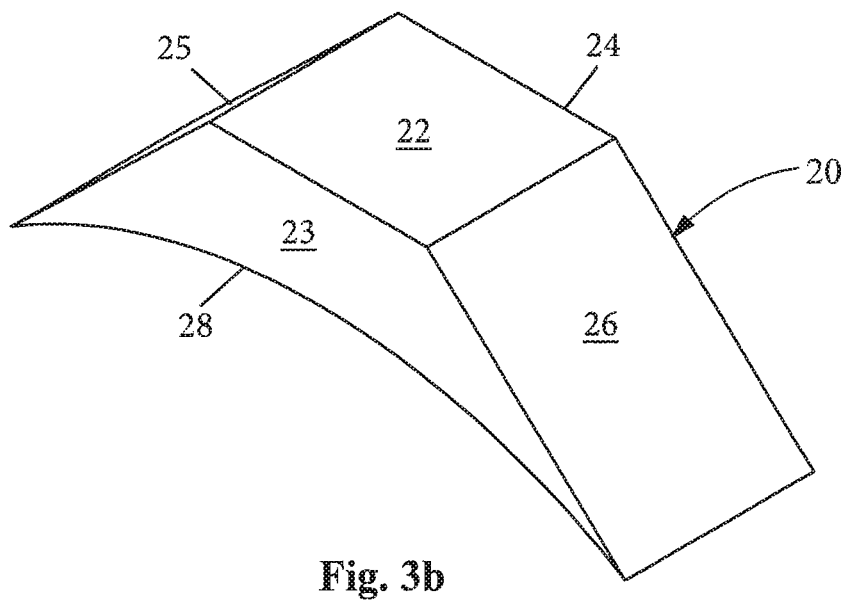

FIG. 1 illustrates the appearance of a flat IDT 40 placed on a curved surface of part 10 and shows the air gaps that the present invention eliminates when in use. In FIG. 1, the contact surface between part 10 and IDT 40 is too small to effectively transfer surface waves generated by the IDT to the curved surface of part 10 for purposes of inspecting the part. FIG. 2 illustrates an IDT 40 that has been mounted on an exemplary embodiment of coupling shoe 20 for allowing surface waves to travel from IDT 40 onto the curved surface of part 10. In the embodiment shown in FIG. 2, coupling shoe 20 includes flat upper/top surface 20, first angled surface 24, second angled surface 26, and lower/bottom surface 28. As indicated by the arrows in FIG. 2, surface waves generated by top-mounted IDT 40 travel from IDT 40 downward and across angled surfaces 25 and 26 and onto the curved surface of part 10. The shape of coupling shoe 20 dramatically increases the contact surface between part 10 and IDT 40 and as shown in FIGS. 3a-b, coupling shoe 20 may be configured for mounting parallel to the longitudinal axis of part 10 (FIG. 3a) or perpendicular to the longitudinal axis of part 10 (FIG. 3b). As shown in FIGS. 3a-3b, each six-sided coupling shoe 20 includes a substantially flat upper surface 22, a first flat side surface 23; a second flat side surface 24 located opposite from the first flat side surface 23; a first angled side surface 25; a second angled side surface 26 located opposite from the first angled side surface 25; and a curved bottom surface 28 located opposite from the substantially flat upper surface 22. Curved bottom surface 28 directly contacts first angled side surface 25 and second angled side surface 26.

FIGS. 4a-c illustrate different possible mounting positions and alternate geometric configurations for coupling shoes 20. In FIG. 4a, coupling shoe 20 is shown in a forward slanting orientation with IDT 40 mounted on an angled top surface. In this embodiment, surface waves generated by IDT 40 travel circumferentially through part 10 in the direction indicated by the arrow inside the circular structure of part 10. In FIG. 4b, coupling shoe 20 is mounted perpendicular to the longitudinal axis of part 10 and IDTs 40, 42, and 44 are mounted on the top surface and angled side surfaces respectively of coupling shoe 20. In this embodiment, surface waves generated by IDTs 40, 42, and 44 travel circumferentially through part 10 in both directions as indicated by the arrows inside the circular structure of part 10. In FIG. 4c, acoustic coupling shoe 20 is mounted parallel with the longitudinal axis of part 10 and the surface waves generated by IDT 40 travel in parallel with the longitudinal axis of part 10 as shown by the arrows in FIG. 4c.

Figure 5:
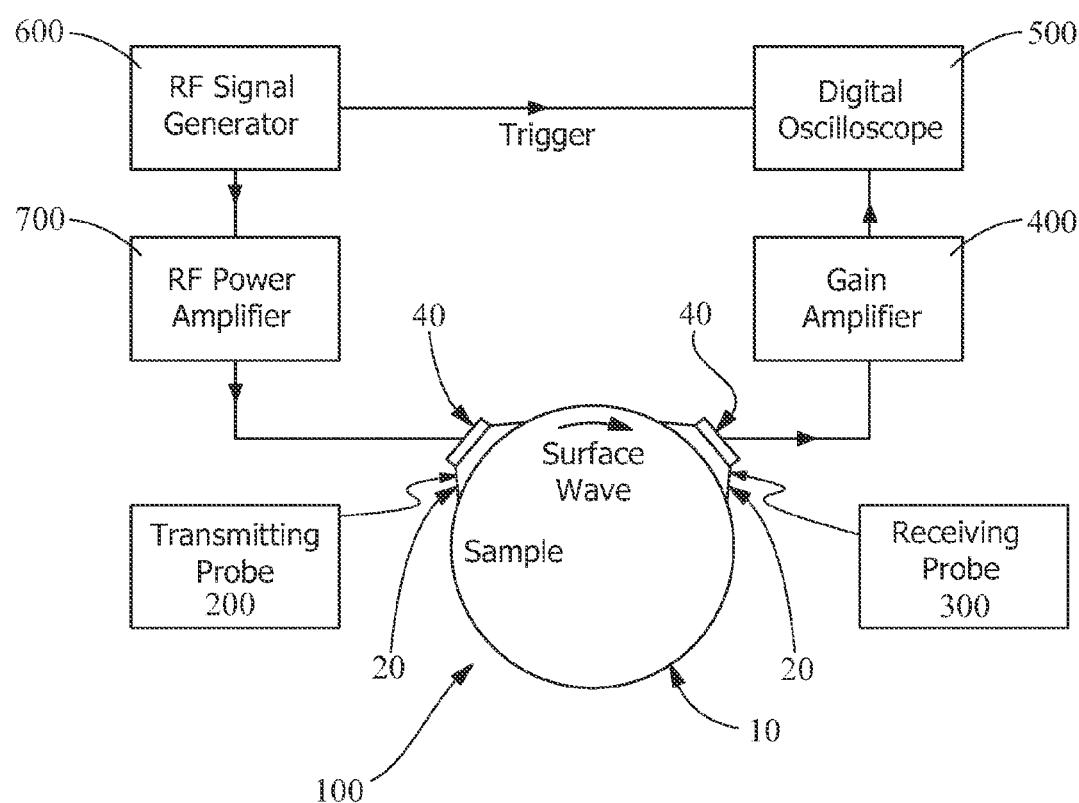
FIG. 5 is a block diagram of an exemplary pitch/catch detection system in accordance with the present invention.

FIG. 5 provides a block diagram of an exemplary pitch/catch detection system in accordance with the present invention. This system includes test assembly 100, which further includes transmitting subassembly 200 and receiving subassembly 300. Both transmitting subassembly 200 and receiving subassembly 300 include at least one coupling shoe 20 and at least one IDT 40. Additional system components include gain amplifier 400; digital oscilloscope 500, RF signal generator 600; and RF power amplifier 700. As shown in FIGS. 6a-b, this system is useful for generating information about the condition of test specimen 100. With reference to FIG. 6a, transmitting subassembly 200 generates a surface wave that travels across the surface of part 10 and that is received by receiving subassembly 300. In this example, the distance between transmitting subassembly 200 and receiving subassembly 300 is about three inches. The received surface wave signal is displayed on a digital oscilloscope screen as shown and the image of the surface wave indicates that part 10 does not include a crack or other problematic structural flaw. With reference to FIG. 6b, transmitting subassembly 200 generates a surface wave that travels across the surface of part 10 toward receiving subassembly 300. However, because a received surface wave signal is not displayed on the digital oscilloscope screen, the conclusion is that a surface breaking crack or other structural flaw is present in part 10 and is reflecting or otherwise preventing receiving subassembly 300 from receiving and displaying the surface wave. Accordingly, the acoustic coupling shoes of the present invention permit accurate characterization of a curved surface using flat IDT sensors.

The coupling shoes of the present invention may be manufactured from metal, plastics, composite materials, polymers, nanomaterials, or various combinations thereof. The coupling shoes may further include incident angles ranging from about 1 to 89 degrees and may be polygonal in shape. Each coupling shoe typically includes least one flat surface and the interdigital transducer is attached to that flat surface. The placement of the coupling shoes and the interdigital transducers on the curved surface determines if the acoustic surface waves are transmitted longitudinally or circumferentially across the object being characterized.

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A system for inspecting the surface of a curved object, comprising:

(a) an object having a curved surface, wherein the object includes a longitudinal axis and a circumference;

(b) at least one substantially flat interdigital transducer, wherein the interdigital transducer is operative to generate surface energy waves; and (c) at least one six-sided coupling device disposed between the curved surface and the substantially flat interdigital transducer, wherein the at least one six-sided coupling device is operative to conform to the curved surface of the object, support the interdigital transducer, and provide a medium through which the surface energy waves can effectively travel from the interdigital transducer to the curved surface and across the curved surface in a predetermined direction, and wherein the at least one six-sided coupling device further includes:

(i) a substantially flat upper surface;
(ii) a first flat side surface;
(iii) a second flat side surface located opposite from the first flat side surface;
(iv) a first angled side surface, wherein the first angled side surface is operative to direct the surface energy waves onto the curved surface of the object in a predetermined direction;
(v) a second angled side surface located opposite from the first angled side surface, wherein the second angled side surface is operative to direct the surface energy waves onto the curved surface of the object in a predetermined direction; and
(vi) a curved lower surface located opposite from the substantially flat upper surface, wherein the curved lower surface directly contacts both the first and second angled side surfaces.

2. The system of claim 1, wherein the interdigital transducer is operative to receive surface energy waves.

3. The system of claim 1, wherein the surface energy waves are acoustic waves.

4. The system of claim 1, wherein the coupling device is polymethyl methacrylate.

5. The system of claim 1, wherein the coupling device further includes metal, plastics, composite materials, polymers, nanomaterials, or combinations thereof.

6. The system of claim 1, wherein the coupling device further includes incident angles ranging from about 1 to 89 degrees.

7. The system of claim 1, wherein the interdigital transducer is mounted on the substantially flat upper surface.

8. The system of claim 1, wherein an interdigital transducer may be mounted on any or all of the surfaces of the six-sided coupling device.

9. A system for inspecting the surface of a curved object, comprising:

(a) an object having a curved surface, wherein the object includes a longitudinal axis and a circumference;

(b) at least one substantially flat interdigital transducer, wherein the interdigital transducer is operative to generate and receive surface acoustic waves; and (c) at least one six-sided coupling device disposed between the curved surface and the substantially flat interdigital transducer, wherein the at least one six-sided coupling device is operative to conform to the curved surface of the object, support the interdigital transducer, and provide a medium through which the surface energy waves can effectively travel from the interdigital transducer to the curved surface and across the curved surface in a predetermined direction, and wherein the at least one six-sided coupling device further includes:

(i) a substantially flat upper surface;
(ii) a first flat side surface;
(iii) a second flat side surface located opposite from the first flat side surface;
(iv) a first angled side surface, wherein the first angled side surface is operative to direct the surface energy waves onto the curved surface of the object in a predetermined direction;
(v) a second angled side surface located opposite from the first angled side surface, wherein the second angled side surface is operative to direct the surface energy waves onto the curved surface of the object in a predetermined direction; and
(vi) a curved lower surface located opposite from the substantially flat upper surface, wherein the curved lower surface directly contacts both the first and second angled side surfaces.

10. The system of claim 9, wherein the coupling device is polymethyl methacrylate.

11. The system of claim 9, wherein the coupling device further includes metal, plastics, composite materials, polymers, nanomaterials, or combinations thereof.

12. The system of claim 9, wherein the coupling device further includes incident angles ranging from about 1 to 89 degrees.

13. The system of claim 9, wherein the interdigital transducer is mounted on the substantially flat upper surface.

14. The system of claim 9, wherein an interdigital transducer may be mounted on any or all of the surfaces of the six-sided coupling device.

15. A six-sided coupling device for transmitting surface energy waves, comprising:

(a) a substantially flat upper surface, wherein the substantially flat upper surface is adapted to receive at least one surface energy wave generating device;
(b) a first flat side surface;
(c) a second flat side surface located opposite from the first flat side surface;
(d) a first angled side surface;
(e) a second angled side surface located opposite from the first angled side surface; and
(f) a curved bottom surface, wherein the curved bottom surface is adapted to conform to a curved surface of an object to be inspected
(g) wherein the first and second angled side surfaces directly contact the curved bottom surface and are operative to direct surface energy waves generated by the at least one surface energy wave generating device onto and across the curved surface of the object to be inspected in a predetermined direction.

16. The device of claim 15, wherein the at least one surface energy wave generating device is an interdigital transducer, and wherein the interdigital transducer is operative to both generate and receive surface acoustic waves.

17. The device of claim 15, wherein the coupling device is polymethyl methacrylate.

18. The device of claim 15, wherein the coupling device further includes metal, plastics, composite materials, polymers, nanomaterials, or combinations thereof.

19. The system of claim 1, wherein the predetermined direction of the surface energy waves directed by the first and second angled side surfaces is parallel to the longitudinal axis of the object having a curved surface.

20. The system of claim 1, wherein the predetermined direction of the surface energy waves directed by the first and second angled side surfaces is perpendicular to the longitudinal axis of the object having a curved surface, and wherein the surface energy waves travel circumferentially through the object.

21. The system of claim 9, wherein the predetermined direction of the surface energy waves directed by the first and second angled side surfaces is parallel to the longitudinal axis of the object having a curved surface.

22. The system of claim 9, wherein the predetermined direction of the surface energy waves directed by the first and second angled side surfaces is perpendicular to the longitudinal axis of the object having a curved surface, and wherein the surface energy waves travel circumferentially through the object.

23. The device of claim 15, wherein the object to be inspected includes a longitudinal axis and wherein the predetermined direction of the surface energy waves directed by the first and second angled side surfaces is parallel to the longitudinal axis of the object to be inspected.

24. The device of claim 15, wherein the object to be inspected includes a longitudinal axis and a circumference, wherein the predetermined direction of the surface energy waves directed by the first and second angled side surfaces is perpendicular to the longitudinal axis of the object to be inspected, and wherein the surface energy waves travel circumferentially through the object.

\* \* \* \* \*